United States Patent [19]

DeWitt et al.

[11] 4,167,572
[45] Sep. 11, 1979

[54] N-6-CHLORONICOTINOYL-D,L-HOMOCYSTEINE THIOLACTONE

[75] Inventors: Paolo DeWitt; Maria T. Ramacci, both of Rome, Italy

[73] Assignee: SIGMA-TAU Industrie Farmaceutiche Riunite S.p.A., Italy

[21] Appl. No.: 837,529

[22] Filed: Sep. 28, 1977

[30] Foreign Application Priority Data

Oct. 14, 1976 [IT] Italy ................. 51734 A/76

[51] Int. Cl.² ................. C07D 213/56; A61K 31/44
[52] U.S. Cl. ................. 424/266; 546/284
[58] Field of Search ................. 260/294.8 D, 295.5 A; 424/266; 546/284

[56] References Cited
U.S. PATENT DOCUMENTS 4,021,433  5/1977  Cavazza ................. 260/294.8 D

OTHER PUBLICATIONS

Burger, Medicinal Chemistry, Second Edition, Interscience Publishers, p. 43, RS 403 B8 1960.

*Primary Examiner*—Alan L. Rotman
*Attorney, Agent, or Firm*—Robert E. Burns; Emmanuel J. Lobato; Bruce L. Adams

[57] ABSTRACT

N-6-chloronicotinoyl-d,l-homocysteine thiolactone of the formula

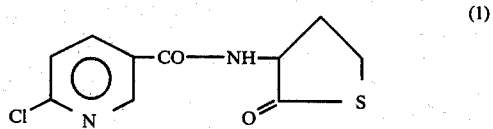

(1)

and method for its preparation are described. The compound has antilipolytic activity and is useful in compositions for treatment of conditions of elevated free fatty acid and triglyceride plasma levels.

3 Claims, No Drawings

N-6-CHLORONICOTINOYL-D,L-HOMOCYSTEINE THIOLACTONE

THE INVENTION

The object of this invention is N-6-chloronicotinoyl-d,l-homocysteine thiolactone

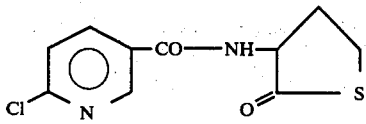
(1)

and its pharmacologically acceptable salts and the methods for the preparation of the compound and its salts and its use.

Compound (1) may be used as such or as a salt with mineral acids, e.g. hydrochloric, sulphuric, phosphoric acid, etc., or with mono- or polycarboxylic aliphatic organic acids, e.g., formic acetic, lactic, succinic, malonic, glutaric, adipic, tartaric, citric, malic, maleic, fumaric acid, etc., or with aromatic acids such as benzoic, salicilic, pamoic acid, etc., or with mandelic, diphenylacetic, benzylic acid, etc., or with sulfonic acids such as methanesulfonic, benzenesulfonic, toluene sulfonic acid, etc., or with sulfamic acids such as cyclamic acid, etc.

Compound (1) and its pharmacologically acceptable salts have shown pharmacological properties characterized by high antilipolitic and good liver protecting activity and with low toxicity.

DETAILED DESCRIPTION

N-6-chloronicotinoyl-d,l-homocysteine thiolactone may be prepared, with high yield, by reacting 6-chloronicotinic chloride hydrochloride with homocysteine thiolactone. (6-chloronicotinic chloride hydrochloride is prepared by adding thionyl chloride to 6-chloronicotinic acid without solvents) in the presence of an excess of pyridine or other proton accepting tertiary organic basic compounds dissolved in an inert, preferably anhydrous organic solvents, e.g. chloroform or dioxane. The reaction takes place at room temperature, is generally exothermic and reaches, without cooling, 50°–60° C.

The reaction is complete in about 2 hours. The mixture resulting from the reaction is cooled and washed several times with $H_2O$, then the solvent is evaporated in vacuo and the solid thus obtained is generally purified by dissolving the precipitate in EtOH, decolorizing upon boiling, with active charcoal, cooling and adding purified water. The resulting solid is the free base (1) which may be converted to the desired salts by means of the above-mentioned acids.

N-6-chloronicotinoyl-d,l-homocysteine thiolactone m.p 164°–166° C. is a white microcrystalline powder stable to heat and light.

Compound (1) and its salts may be administered in effective amounts both as such and together with or as a mixture with a suitable excipient according to the route of administration and current pharmaceutical practice, as is well known to the art. Compound (1) and its pharmacologically acceptable salts may be administered in single or divided doses via the oral route in the form of tablets containing excipients such as lactose or starch, etc., or in capsules, as such or with excipients, or in the form of elixir or suspensions containing aromatizing colouring agents and various excipients.

Compound (1) and its pharmaceutically acceptable salts may be injected via the parenteral route in effective dosage amounts, e.g. via the intramuscular or intravenous routes; in the case of such administrations Compound (1) by its pharmaceutically acceptable salts may be employed more effectively in the form of sterile aqueous solutions which may contain other dissolved substances, e.g. salts or glucose, in sufficient quantity to make the solutions isotonic.

The pharmaceutic compositions containing N-6-chloronicotinoyl-d,l-homocysteine thiolactone in effective amounts in combination with one or more therapeutically active agents form part of this invention to all intents and purposes. The following examples illustrate the invention, without however restricting the invention itself.

EXAMPLE 1

N-6-chloronicotinoyl-d,l-homocysteine thiolactone

To 15.7 g(0.01 moles) of 6-chloronicotinic acid add 15 ml (0.02 moles) of thionyl chloride ($SOCl_2$) dropwise and allow to reflux for about 2 hours; when the solution is clear evaporate the excess thionyl chloride in vacuo and the resulting yellow liquid is added dropwise to a suspension of 250 ml of chloroform, 15.4 g(0.01 moles) of homocysteine thiolactone hydrochloride and 16 ml (0.02 moles) of pyridine.

This reaction is carried out at room temperature, however a rise in temperature up to 50°–60° C. is noted. The reaction is complete after keeping the mixture under vigorous agitation for about 2 hours. Cool the mixture to 15° C. and wash with 3 portions of purified water (150 ml×3), discard washing waters and evaporate the organic phase to dryness in vacuo. An amorphous pale yellow solid is thus obtained; dissolve in 300 ml of EtOH and treat with active charcoal; allow to reflux for 20 minutes, cool, concentrate at half volume and add purified water until incipient precipitation. The resulting white solid (18.7 g) melts at 164°–166° C. and corresponds to formula (1).

EXAMPLE 2

Pharmacological activity of N-6-chloronicotinoyl-d,l-homocysteine thiolactone

The new compound has an LD $50>3000$ mg $kg^{-1}$ orally in rats; 2700 mg $kg^{-1}$ orally in mice. It has shown the following characteristics of pharmacological activity in laboratory animals:

(1) Antilipolitic activity (1.1) In lipolysis induced by fasting (17 hours), 200 mg $kg^{-1}$ of the compound in rats reduce, 1 hour after administration, the FFA (Free Fatty Acids) and triglyceride plasma levels by 64% and 50% respectively.

(1.2) In NA injection (Nor-Adrenaline 1 mg $kg^{-1}$ subcutaneously)-induced lipid mobilization in rats, 200 mg $kg^{-1}$ of the compound reduce FFA plasma levels by 74% one hour after treatment.

(2) Liver-protecting activity (2.1) In d-l Ethionine (1 g $kg^{-1}$ orally)-induced liver damage in rats, the compound given at the dose regimen of 200 mg $kg^{-1}$ orally normalizes the FFA liver levels which were increased by the toxic agent.

The pharmacological activities of the compound as described above, was investigated according to the methods described in the following articles:

(1) Definition of LD 50:

(1.1) J. T. Litchfield Jr., F. Wilcoxon, A simplified method of evaluating dose-effect experiments, J. Pharmacol. Exp. Therap., 94, 99–113, 1949.

(2) Activity upon lipolysis during fasting:

(2.1) L. A. Carlson, E. R. Nye, Acute effect of Nicotinic acid in the rat. Plasma and liver lipids and blood glucose, Acta Medica Scand., 179, 453, 1966.

(2.2) C. Dalton, C. Van Trabert, J. X. Dwyer, Relationship of Nicotinamide and Nicotinic acid to hypolipidemia, Bioch. Pharmacol., 19, 2609, 1970.

(2.3) A. Bizzi, S. Garattini, Drugs lowering plasma free fatty acids: similarities and dissimilarities with Nicotinic acid effect, p. 207. K. F. Gey and L. A. Carlson Edrs., Hans Huber Publisher, Bern Stuttgard Vienna, 1971.

(3) Activity upon NA-induced lipolysis:

(3.1) S. Garattini, A. Bizzi, Inibiteurs de la mobilization des acides gras libres, Actualité Pharmacol., XXII Serie, 169, 1969.

(4) Activity upon d-l ethionine-induced liver damage;

(4.1) E. Farber, M.D., B. Lombardi, etc.

The prevention by Adenosine triphosphate of the fatty liver induced by Ethionine, Laboratory Investigation, 12, (9), 873–883, 1963.

(4.2) N. M. Alexander, R. Scheig etc., Effect of L-Asparagine and related compounds on the hepatic fatty infiltration and necrosis induced by ethionine and $CCl_4$, Biochem. Pharmacol., 16, 1091–1097, 1967.

What we claim is:

1. N-6-chloronicotinoyl-d,l-homocysteine thiolactone having lipolytic activity:

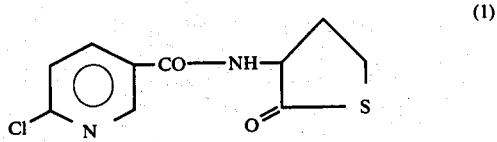

(1)

and its pharmacologically acceptable salts.

2. A method for reducing elevated free fatty acid and triglyceride plasma levels which comprises the steps of administering to individual exhibiting such elevated levels an effective amount of a composition containing the compound according to claim 1.

3. A composition having antilipolytic activity comprising the compound, N-6-chloronicotinoyl-d,l,homocysteine thiolactone or its pharmacologically acceptable salts according to claim 1 in dosage form in a suitable pharmaceutical vehicle.

* * * * *